United States Patent
Thomasson

(10) Patent No.: US 6,683,114 B2
(45) Date of Patent: Jan. 27, 2004

(54) TREATMENT OF PSORIASIS

(75) Inventor: Holly Read Thomasson, Indianapolis, IN (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 10/203,403

(22) PCT Filed: Feb. 20, 2001

(86) PCT No.: PCT/US01/05260

§ 371 (c)(1),
(2), (4) Date: Aug. 7, 2002

(87) PCT Pub. No.: WO01/66101

PCT Pub. Date: Sep. 13, 2001

(65) Prior Publication Data

US 2003/0045585 A1 Mar. 6, 2003

Related U.S. Application Data

(60) Provisional application No. 60/187,508, filed on Mar. 7, 2000.

(51) Int. Cl.$^7$ .................. A61K 31/135; A61K 31/165; A61K 31/535; A61K 31/38
(52) U.S. Cl. .................. 514/651; 514/231.2; 514/649; 514/624; 514/438
(58) Field of Search .............. 514/651, 231.2, 514/649, 624, 438

(56) References Cited

U.S. PATENT DOCUMENTS

| | | | | |
|---|---|---|---|---|
| 4,424,223 A | * | 1/1984 | Keve et al. | 514/283 |
| 5,508,276 A | * | 4/1996 | Anderson et al. | 514/183 |
| 5,532,244 A | * | 7/1996 | Wong et al. | 514/255.03 |
| 5,658,590 A | * | 8/1997 | Heiligenstein et al. | 424/464 |
| 5,916,910 A | * | 6/1999 | Lai | 514/423 |
| 6,028,070 A | * | 2/2000 | Heiligenstein | 514/238.8 |
| 6,150,396 A | * | 11/2000 | Iyengar et al. | 514/438 |
| 6,197,828 B1 | * | 3/2001 | Jerussi et al. | 514/648 |
| 6,342,533 B1 | * | 1/2002 | Jerussi et al. | 514/649 |
| 6,352,986 B1 | * | 3/2002 | Hassan et al. | 514/231.2 |
| 6,403,645 B2 | * | 6/2002 | Schildkraut et al. | 514/567 |
| 6,583,142 B2 | * | 6/2003 | Crocker et al. | 514/241 |

OTHER PUBLICATIONS

Alpsoy, E. et al. *Is the Efficacy of Topical Corticosteroid Therapy for Psoriasis Vulgaris Enhanced by Concurrent Moclobemide Therapy?*, J. Am. Acad. Dermatol. (1998), 38(2) :197–200.

Stiefelhagen, P., *Progress and Education in Medicine. Part II: Depressive Disorders, Possibilities for Prenatal Therapy, Autoimmune Diseases and Drug Therapy*, Internist (1999) 40(6) :686–91.

Hopkins, S., *A Year of Therapeutic Advances*, Manufacturing Chemist (1998) 69(4) :16–17, 21.

Riley, T.N. et al, *Major Drugs Highlights '94*, U.S. Pharmacist (1994) 19(10) :55–63, 67–82, 86–87, 91–104.

* cited by examiner

Primary Examiner—Vickie Kim
(74) Attorney, Agent, or Firm—Charles E. Cohen; Robert D. Titus

(57) ABSTRACT

Norepinephrine reuptake inhibitors are used to treat psoriasis.

9 Claims, No Drawings

TREATMENT OF PSORIASIS

This application claims the benefit of provisional application No. 60/187,508, filed Mar. 7, 2000.

FIELD OF THE INVENTION

The invention belongs to the fields of pharmaceutical chemistry and dermatological medicine, and provides a method of treatment of the dermatological disorder known as psoriasis.

BACKGROUND OF THE INVENTION

Psoriasis is a chronic, painful skin disorder that affects more than 7 million Americans. With as many as 250,000 new cases occurring each year, psoriasis typically does not discriminate on the basis of the age or gender of its victims. The disorder occurs slightly more often in women than men, and it has been reported to present itself initially from birth to the age of 90 years. Psoriasis exacts a heavy societal burden in terms of both patient suffering and costs. Annual outpatient treatment of psoriasis was estimated in 1999 to be from $1.6 to $3.2 billion, with over 1.5 million patients seen annually for this disorder by U.S. physicians.

Treatment options currently available to patients suffering from psoriasis include a variety of topical medications, phototherapies, and internal medications. Topical treatments include steroids, coal tar, anthralin, vitamin D3 and analogs, retinoids, and sunshine. Side effects associated with the use of these topical treatments include skin thinning, stretch marks, burns, irritation, and photosensitivity. The use of steroids may also lead to resistance, rendering subsequent steroid treatment ineffective. Phototherapy encompasses the medically supervised administration of ultraviolet light B or psoralen in combination with ultraviolet light A. Long term use of phototherapies may prematurely age the skin and increase the incidence of skin cancers. Internal medications, typically reserved for the most serious cases of psoriasis, include the administration methotrexate, oral retinoids, and cyclosporine. The use of methotrexate requires careful monitoring to avoid liver damage. Use of oral retinoids must be carefully controlled in women because of the potential for severe birth defects. This risk extends for years after the use of the drug has been terminated. Cyclosporine, an immunosuppresant, is reserved for patients that have failed other internal treatments, or for whom the other internal treatments are contraindicated. Rotating between therapies, and combinations of topical medications with phototherapies, have also been found to be useful regimens in the treatment of psoriasis.

There is no cure for psoriasis, and not all patients respond to or tolerate currently available therapies. New treatment options for psoriasis, with improved efficacy, safety, and side effect profiles, are needed.

SUMMARY OF THE INVENTION

The present invention provides a method of treating psoriasis comprising the administration to a patient in need of such treatment of an effective amount of a norepinephrine reuptake inhibitor.

This invention also provides the use of a norepinephrine reuptake inhibitor for the manufacture of a medicament for the treatment of psoriasis. Additionally, this invention provides a pharmaceutical formulation adapted for the treatment of psoriasis containing a norepinephrine reuptake inhibitor.

DETAILED DESCRIPTION

Many compounds, including those discussed at length below, are norepinephrine reuptake inhibitors, and no doubt many more will be identified in the future. In the practice of the present invention, it is intended to include reuptake inhibitors which show 50% effective concentrations of about 1000 nM or less, in the protocol described by Wong et al., *Drug Development Research*, 6, 397 (1985). The norepinephrine reuptake inhibitors useful for the method of the present invention are characterized in being selective for the inhibition of neurotransmitter reuptake relative to their ability to act as direct agonists or antagonists at other receptors. Norepinephrine reuptake inhibitors useful for the method of the present invention include, but are not limited to:

Tomoxetine, (R)-(−)-N-methyl-3-(2-methylphenoxy)-3-phenylpropylamine, is usually administered as the hydrochloride salt. Tomoxetine was first disclosed in U.S. Pat. No. 4,314,081. The word "tomoxetine" will be used here to refer to any acid addition salt or the free base of the molecule. See, for example, Gehlert, et al., *Neuroscience Letters*, 157, 203–206 (1993), for a discussion of tomoxetine's activity as a norepinephrine reuptake inhibitor;

The compounds of formula I:

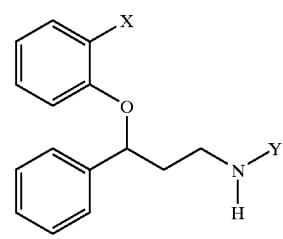

wherein X is $C_1$–$C_4$ alkylthio, and Y is $C_1$–$C_2$ alkyl or a pharmaceutically acceptable salt thereof. The compounds of formula I were described in U.S. Pat. No. 5,281,624, of Gehlert, Robertson, and Wong, and in Gehlert, et al., *Life Sciences*, 55(22), 1915–1920, (1995). The compounds are there taught to be inhibitors of norepinephrine reuptake in the brain. It is also explained that the compounds exist as stereoisomers, and that they accordingly include not only the racemates, but also the isolated individual isomers as well as mixtures of the individual isomers. For example, the compounds of formula I include the following exemplary species:

N-ethyl-3-phenyl-3-(2-methylthiophenoxy)propylamine benzoate;

(R)-N-methyl-3-phenyl-3-(2-propylthiophenoxy)-propylamine hydrochloride;

(S)-N-ethyl-3-phenyl-3-(2-butylthiophenoxy) propylamine;

N-methyl-3-phenyl-3-(2-ethylthiophenoxy)propylamine malonate;

(S)-N-methyl-3-phenyl-3-(2-tert-butylthiophenoxy)-propylamine naphthalene-2-sulfonate;

(R)-N-methyl-3-(2-methylthiophenoxy)-3-phenyl-propylamine;

Reboxetine (Edronax™), 2-[α-(2-ethoxy) phenoxybenzyl]morpholine, is usually administered as the racemate. It was first taught by U.S. Pat. No. 4,229,449, which describes its utility for the treatment of depression. Reboxetine is a selective norepinephrine reuptake inhibitor. The term "reboxetine" will be used here to refer to any acid addition salt or the free base of the molecule existing as the racemate or either enantiomer;

Duloxetine, N-methyl-3-(1-naphthalenyloxy)-3-(2-thienyl)propanamine, is usually administered as the hydrochloride salt and as the (+) enantiomer. It was first taught by U.S. Pat. No. 4,956,388, which shows its high potency. The word "duloxetine" will be used here to refer to any acid addition salt or the free base of the molecule. A preferred duloxetine enteric formulation is a pellet formulation comprising a) a core consisting of duloxetine and a pharmaceutically acceptable excipient; b) an optional separating layer; c) an enteric layer comprising hydroxypropylmethylcellulose acetate succinate (HPMCAS) and a pharmaceutically acceptable excipient; d) an optional finishing layer. This formulation is taught in U.S. Pat. No. 5,508,074;

Venlafaxine is known in the literature, and its method of synthesis and its activity as an inhibitor of serotonin and norepinephrine uptake are taught by U.S. Pat. No. 4,761,501. Venlafaxine is identified as compound A in that patent; and Milnacipran (N,N-diethyl-2-aminomethyl-1-phenylcyclopropanecarboxamide is taught by U.S. Pat. No. 4,478,836, which prepared milnacipran as its Example 4. The patent describes its compounds as antidepressants. Moret et al., *Neuropharmacology* 24, 1211–19 (1985), describe its pharmacological activities as an inhibitor of serotonin and norepinephrine reuptake.

All of the U.S. patents mentioned above in connection with compounds and formulations used in the present invention are incorporated herein by reference.

While all compounds exhibiting norepinephrine reuptake inhibition are useful for the method of the present invention, certain are preferred. It is preferred that the norepinephrine reuptake inhibitor is selective for norepinephrine over other neurotransmitters. It is also preferred that the norepinephrine reuptake inhibitor is selected from tomoxetine, reboxetine, or a compound of formula I. It is especially preferred that the norepinephrine reuptake inhibitor be selected from tomoxetine, reboxetine, or (R)-N-methyl-3-(2-methylthiophenoxy)-3-phenylpropylamine. The use of tomoxetine hydrochloride for the treatment of psoriasis is the most preferred embodiment of the present invention.

It will be understood by the skilled reader that most or all of the compounds used in the present invention are capable of forming salts, and that the salt forms of pharmaceuticals are commonly used, often because they are more readily crystallized and purified than are the free bases. In all cases, the use of the pharmaceuticals described above as salts is contemplated in the description herein, and often is preferred, and the pharmaceutically acceptable salts of all of the compounds are included in the names of them.

Many of the compounds used in this invention are amines, and accordingly react with any of a number of inorganic and organic acids to form pharmaceutically acceptable acid addition salts. Since some of the free amines of the compounds of this invention are typically oils at room temperature, it is preferable to convert the free amines to their pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, b-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid.

Administration

The dosages of the drugs used in the present invention must, in the final analysis, be set by the physician in charge of the case using knowledge of the drugs, the properties of the drugs in combination as determined in clinical trials, and the characteristics of the patient including diseases other than that for which the physician is treating the patient. General outlines of the dosages, and some preferred dosages, can and will be provided here.

Tomoxetine: from about 5 mg/day to about 200 mg/day; preferably in the range from about 60 to about 150 mg/day; more preferably from about 60 to about 130 mg/day; and still more preferably from about 60 to about 120 mg/day;

Compounds of formula I: from about 0.01 mg/kg to about 20 mg/kg; preferred daily doses will be from about 0.05 mg/kg to 10 mg/kg; ideally from about 0.1 mg/kg to about 5 mg/kg;

Reboxetine: from about 1 to about 30 mg, once to four times/day; preferred, from about 5 to about 30 mg once/day;

Duloxetine: from about 1 to about 30 mg once/day; preferred, from about 5 to about 20 mg once/day;

Venlafaxine: from about 10 to about 150 mg once-thrice/day; preferred, from about 25 to about 125 mg thrice/day; and Milnacipran: from about 10 to about 100 mg once-twice/day; preferred, from about 25 to about 50 mg twice/day.

All of the compounds concerned are orally available and are normally administered orally, and so oral administration is preferred. However, oral administration is not the only route or even the only preferred route. For example, transdermal administration may be very desirable for patients who are forgetful or petulant about taking oral medicine. The drugs may also be administered by the percutaneous, intravenous, intramuscular, intranasal or intrarectal route, in particular circumstances. The route of administration may be varied in any way, limited by the physical properties of the drugs and the convenience of the patient and the caregiver. The following examples illustrate formulations useful for the administration of norepinephrine reuptake inhibitors, and are not intended to limit the scope of the present invention in any way.

Formulation Example 1

| Hard Gelatin Capsules | |
|---|---|
| Ingredient | Quantity (mg/capsule) |
| Tomoxetine hydrochloride | 30.0 |
| Starch | 305.0 |
| Magnesium stearate | 5.0 |

The above ingredients are mixed and filled into hard gelatin capsules in 340 mg quantities.

Formulation Example 2

| Tablet | |
|---|---|
| Ingredient | Quantity (mg/tablet) |
| Tomoxetine hydrochloride | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

| Dry Powder Inhaler | |
|---|---|
| Ingredient | Weight % |
| Tomoxetine hydrochloride | 5 |
| Lactose | 95 |

The active ingredient is mixed with the lactose and the mixture is added to a dry powder inhaling appliance.

Formulation Example 4

| Tablet | |
|---|---|
| Ingredient | Quantity (mg/tablet) |
| Tomoxetine hydrochloride | 30.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C.–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

| Capsules | |
|---|---|
| Ingredient | Quantity (mg/capsule) |
| Tomoxetine hydrochloride | 40.0 |
| Starch | 109.0 |
| Magnesium stearate | 1.0 |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

| Suppositories | |
|---|---|
| Ingredient | Amount |
| Tomoxetine hydrochloride | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

| Suspensions | |
|---|---|
| Ingredient | Amount |
| Tomoxetine hydrochloride | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and color | q.v. |
| Purified water to | 5.0 ml |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

| Capsules | |
|---|---|
| Ingredient | Quantity (mg/capsule) |
| Tomoxetine hydrochloride | 15.0 |
| Starch | 407.0 |
| Magnesium stearate | 3.0 |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Example 9

| Intravenous Formulation | |
|---|---|
| Ingredient | Quantity |
| Tomoxetine hydrochloride | 250.0 mg |
| Isotonic saline | 1000 ml |

Formulation Example 10

| Topical Formulation | |
|---|---|
| Ingredient | Quantity |
| Tomoxetine hydrochloride | 1–10 g |
| Emulsifying wax | 30 g |
| Liquid paraffin | 20 g |
| White soft paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

| Sublingual or Buccal Tablets | |
|---|---|
| Ingredient | Quantity (mg/tablet) |
| Tomoxetine hydrochloride | 10.0 |
| Glycerol | 210.5 |
| Water | 143.0 |
| Sodium citrate | 4.5 |
| Polyvinyl alcohol | 26.5 |
| Polyvinylpyrrolidone | 15.5 |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the active ingredient is slowly admixed. The homogenous mixture is poured into forms made of an inert material to produce a drug-containing diffusion matrix having a thickness of about 2–4 mm. This diffusion matrix is then cut to form individual tablets having the appropriate size.

Psoriasis is a chronic skin disorder of unknown causation, characterized by inflamed skin lesions. A number of different types of psoriasis have been identified, and are described in the following paragraphs.

Erythrodermic psoriasis is an inflamed lesion of the skin with fine scales, and is frequently accompanied by severe pain, itching, and possibly swelling.

Guttate psoriasis is characterized by the appearance of small red dots of psoriasis, typically occurring on the arms, legs, and trunk of the patient.

Inverse psoriasis is inflamed lesions without scales, typically appearing at the armpit, groan, under the breast, and other skin folds.

Plaque psoriasis, the most commonly observed variety, is characterized by inflamed lesions covered with a silvery white scale. Although plaque psoriasis may occur on any skin surface, it is most commonly found on the knees, elbows, scalp, and trunk.

Pustular psoriasis is characterized by the appearance of blister-like lesions of non-infectious pus. The lesions may be localized or widespread over the skin.

Psoriasis may also present itself as pits in toenails and fingernails. The pitting may be accompanied by discoloration and thickening of the nail, and the nail may detach from the nail bed.

Psoriasis is also categorized by degree based upon the prevalence of the lesions. Patients with lesions over less than 2% of their body are considered to have mild psoriasis. Patients with lesions occurring on from 2%–10% of their bodies are considered to have moderate psoriasis, while patients with lesions covering over 10% of their bodies are considered to have severe psoriasis.

The method of the present invention is useful for the treatment of all forms and degrees of psoriasis.

Inhibition or Norepinephrine Reuptake

The ability of compounds to inhibit the reuptake of norepinephrine may be measured by the general procedure of Wong, et al., supra.

Male Sprague-Dawley rats weighing 150–250 gm are decapitated and brains are immediately removed. Cerebral cortices are homogenized in 9 volumes of a medium containing 0.32 M sucrose and 10 mM glucose. Crude synaptosomal preparations are isolated after differential centrifugation at 1000×g for 10 minutes and 17,000×g for 28 minutes. The final pellets are suspended in the same medium and kept in ice until use within the same day.

Synaptosomal uptake of $^3$H-norepinephrine is determined as follows. Cortical synaptosomes (equvalent to 1 mg of protein) are incubated at 37° C. for 5 minutes in 1 mL Krebs-bicarbonate medium containing also 10 mM glucose, 0.1 mM iproniazide, 1 mM ascorbic acid, 0.17 mM EDTA and 50 nM $^3$H-norepinephrine. The reaction mixture is immediately diluted with 2 mL of ice-chilled Krebs-bicarbonate buffer and filtered under vacuum with a cell harvester (Brandel, Gaithersburg, Md.). Filters are rinsed twice with approximately 5 mL of ice-chilled 0.9% saline and the uptake of $^3$H-norepinephrine assessed by liquid scintillation counting. Accumulation of $^3$H-norepinephrine at 4° C. is considered to be background and is subtracted from all measurements. The concentration of the test compound required to inhibit 50% of the $^3$H-norepinephrine accumulation ($IC_{50}$ values) are determined by linear regression analysis.

EXAMPLE 1

The subject, a 39-year-old Caucasian male, presented with moderately severe plaque-like psoriasis of his legs. The subject had suffered from psoriasis for most of his life, and the condition had worsened immediately prior to the present study. The lesions had been treated with topical steroids, including Temovate™ ((11β, 16β)-21-chloro-9-fluoro-11,17-dihydroxy-16-methylpregna-1,4-diene-3,20-dione, Glaxo), many times prior to the present study without success. The subject was treated with 60 mg of tomoxetine hydrochloride, twice daily for 12 consecutive days. At the time of final assessment the subject demonstrated significant improvement, with only a few scales and faintly erythematous skin at the sites of the previous lesions.

I claim:

1. A method of treating psoriasis comprising administering to a patient in need of such treatment an effective amount of a norepinephrine reuptake inhibitor, wherein the norepinephrine reuptake inhibitor is selected from the group consisting of tomoxetine, reboxetine, duloxetine, venlafaxine, milnacipran, and a compound of formula I:

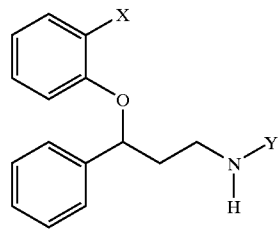

Wherein X is $C_1$–$C_4$ alkylthio, and Y is $C_1$–$C_2$ alkyl or a pharmaceutically acceptable salt thereof.

2. A method of claim 1 wherein the norepinephrine reuptake inhibitor is tomoxetine, reboxetine, or a compound of formula I.

3. A method of claim 2 wherein the norepinephrine reuptake inhibitor is tomoxetine.

4. A method of claim 2 wherein the norepinephrine reuptake inhibitor is tomoxetine hydrochloride.

5. A method of claim 2 wherein the norepinephrine reuptake inhibitor is reboxetine.

6. A method of claim 2 wherein the norepinephrine reuptake inhibitor is (R)-N-methyl-3-(2-methylthiophenoxy)-3-phenylpropylamine.

7. A method of claim 1 wherein plaque psoriasis is treated.

8. A method of claim 7 wherein the norepinephrine reuptake inhibitor is tomoxetine.

9. A method of claim 7 wherein the norepinephrine reuptake inhibitor is tomoxetine hydrochloride.

* * * * *